United States Patent [19]

Worsch

[11] Patent Number: 5,144,038

[45] Date of Patent: Sep. 1, 1992

[54] PROCESS FOR THE PRODUCTION OF 2-HYDROXY-3-HALO-5-NITROPYRIDINES

[75] Inventor: Detlev Worsch, Brigerbad, Switzerland

[73] Assignee: Lonza Ltd., Gampel/Valais, Switzerland

[21] Appl. No.: 731,334

[22] Filed: Jul. 17, 1991

[30] Foreign Application Priority Data

Jul. 17, 1990 [CH] Switzerland .................. 2373/90

[51] Int. Cl.$^5$ .................. C07D 213/72; C07D 213/55
[52] U.S. Cl. ...................... 546/297; 546/298
[58] Field of Search .......................... 546/297

[56] References Cited

U.S. PATENT DOCUMENTS 3,495,969  2/1970  Driscoll .................. 71/94

FOREIGN PATENT DOCUMENTS 3545570  6/1987  Fed. Rep. of Germany ...... 546/297
664754  3/1988  Switzerland .................. 546/297

OTHER PUBLICATIONS

Chemical Abstracts, 70:106327 (which is an abstract of Batkowski, T., Rocz. Chem., 42, (2), (1968) pp. 2079 to 2088).

*Primary Examiner*—Alan L. Rotman
*Attorney, Agent, or Firm*—Fisher, Christen & Sabol

[57] ABSTRACT

A process for the production of 2-hydroxy-3-halo-5-nitropyridines, in which a 5-halo-6-hydroxynicotinic acid is nitrated in the end product. The resultant pyridines form valuable intermediate products for active ingredient synthesis.

7 Claims, No Drawings

PROCESS FOR THE PRODUCTION OF 2-HYDROXY-3-HALO-5-NITROPYRIDINES

BACKGROUND OF THE INVENTION

1. Field Of The Invention

The invention relates to a process for the production of 2-hydroxy-3-halo-5-nitropyridines.

2. Background Art

Due to the reactive functional groups, 2-hydroxy-3-halo-4-nitropyridines are universally applicable for active ingredient syntheses for pharmaceutical agents or herbicides. For example, 2,3-dichloro-5-nitropyridine, obtained by chlorination according to *Chemical Abstracts*, 70:106327x, [T. Batkowski, Rocz. Chem., 42, (2), (1968), pp. 2079 to 2088], can be used for synthesis of herbicides according to German OS 3,545,570. According to *Chemical Abstracts*, 70:106327x, [T. Batkowski. Rocz. Chem., 42, (2), (1968), pp. 2079 to 2088], it was known to produce 2-hydroxy-3-chloro-5-nitropyridine, starting from 2-amini-5-nitropyridine, by chlorination to 2-amino-3-chloro-5nitropyridine (yield 29 percent) and by subsequent diazotation/saponification of the amino group (yield 72 percent). The unfavorable yields as well as the very difficulty of obtaining feedstock 2-amino-3-chloro-5-nitropyridine are disadvantages of such process.

BROAD DESCRIPTION OF THE INVENTION

The main object of the invention is to provide a process for the production of 2-hydroxy-3-halo-5-nitropyridines which does not suffer the above-described disadvantages. Other objects and advantages of the invention are set out herein or are obvious herefrom to one ordinarily skilled in the art.

The objects and advantages of the invention are achieved by the invention process.

The invention involves a process for the production of 2-hydroxy-3-halo-5-nitropyridines of the general formula:

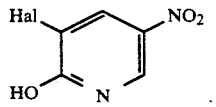

I wherein Hal means chloride, bromine or iodine. A 5-halo-6-hydroxynicotinic acid of the general formula:

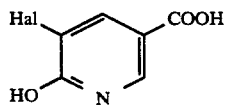

II wherein Hal has the above meaning, is nitrated in the presence of nitric acid and sulfuric acid to provide the designated product.

DETAILED DESCRIPTION OF THE INVENTION

5-Halo-6-hydroxynicotinic acid, preferably 5-chloro-6-hydroxynicotinic acid, can be produced in a simple way from 6-hydroxynicotinic acid, which is available on an industrial scale, by reaction with an acid halide and subsequent hydrolysis of the resultant 5-halo-6-hydroxynicotinic acid halide according to Swiss Patent No. 664,754.

The reaction according to the invention suitably takes place at temperatures between 0° and 100° C., preferably between 40. and 55° C.

Mixtures of concentrated nitric acid and concentrated sulfuric acid in the ratio of 4 to 1, preferably in the ratio of 1 to 1, are suitably used. But mixtures with less sulfuric acid can also be used.

After a reaction time of about 1 to 3 hours, the reaction mixture can be worked up in the usual way, preferably by being taken up in ice water, filtering the resultant suspension and drying the filtered material.

In this way the resulting 2-hydroxy-3-halo-5-nitropyridines can be obtained in high purity and good yield.

EXAMPLE 200 ml of nitric acid (70 percent) was introduced and cooled to 5° C. 200 ml of concentrated sulfuric acid was slowly added with stirring at 5° to 10° C. Then, 100 g (0.576 mol) of 5-chloro-6-hydroxynicotinic acid was slowly introduced at 5° C. The mixture was heated to 50° C. After quieting down the exothermic reaction, it was allowed to stand for another 2 hours at 50° C. and then cooled to room temperature. The mixture was poured in 1.5 l of ice water and the obtained suspension was cooled to $-10°$ C. The suspension was subjected to suction; and the filter residue was washed to pH-neutral with water and dried in a vacuum overnight. 74.4 g of a pale yellow powder was obtained. The yield of product was 74 percent. Other data regarding the product was:

$^1$N-NMR: (DMSO d$_6$, 300 MHz) $\delta$ in ppm; 8.45 (d, 3 Hz, Ar-H); 8.72 (d, 3 Hz, Ar-H); 13.25 (broad, -OH).

Elementary analysis for C$_5$H$_3$N$_2$O$_3$Cl (174.54): Cld: C 34.4%; H 1.7%; N 16.1%; Fnd: C 34.7%; H 1.6%; N 16.5%.

What is claimed is:

1. Process for the production of 2-hydroxy-3-halo-5nitropyridines of the formula:

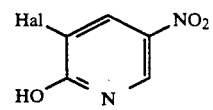

I wherein Hal is chlorine, bromine or iodine, comprising nitrating a 5-halo-6-hydroxynicotinic acid of the formula:

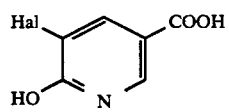

II wherein Hal has the above meaning, in the presence of nitric acid and sulfuric acid.

2. Process according to claim 1 wherein the nitration is performed at a temperature between 0° and 100° C.

3. Process according to claim 2 wherein the nitration is performed with a mixture of concentrated nitric acid and concentrated sulfuric acid in a ratio of 4:1 to 1:1.

4. Process according to claim 1 wherein the nitration is performed with a mixture of concentrated nitric acid and concentrated sulfuric acid in a ratio of 4:1 to 1:1.

5. Process according to claim 1 wherein the nitration is performed at a temperature between 40° and 55° C.

6. Process according to claim 1 wherein the nitration is conducted for about 1 to 3 hours.

7. Process according to claim 1 wherein Hal in formula I and in formula II is chlorine.

* * * * *